(12) United States Patent
Combs

(10) Patent No.: US 8,658,428 B2
(45) Date of Patent: Feb. 25, 2014

(54) METHODOLOGY FOR DETERMINATION OF NITROGEN CONTENT IN NITROCELLULOSE

(75) Inventor: Michael T. Combs, Shady Spring, WV (US)

(73) Assignee: Alliant Techsystems Inc., Minneapolis, MN (US)

( * ) Notice: Subject to any disclaimer, the term of this patent is extended or adjusted under 35 U.S.C. 154(b) by 292 days.

(21) Appl. No.: 13/175,503

(22) Filed: Jul. 1, 2011

(65) Prior Publication Data

US 2013/0000382 A1    Jan. 3, 2013

(51) Int. Cl.
*B01D 15/08* (2006.01)

(52) U.S. Cl.
USPC .......... 436/106; 436/174; 436/177; 436/178; 210/634; 210/656; 210/660; 73/61.41; 73/61.52; 73/61.55

(58) Field of Classification Search
USPC .......... 436/106, 174, 177, 178; 210/634, 656, 210/660; 73/61.41, 61.52, 61.55
See application file for complete search history.

(56) References Cited

U.S. PATENT DOCUMENTS

| 6,527,887 B1 | 3/2003 | Ruebner et al. |
| 2007/0068610 A1 | 3/2007 | Nickel |

FOREIGN PATENT DOCUMENTS

EP    1752766    2/2007

OTHER PUBLICATIONS von Roedern, "A new method for the characterization of chemical libraries—solely by HPLC retention times", Molecular Diversity, 3: 253-256, 1998.*
Verschragen et al: "Comparative investigation of some methods for the determination of the nitrogen content of nitrocellulose" Analytica Chimica Acta, Elsevier, Amsterdam, NL. vol. 12, Jan. 1, 1955 pp. 227-230, XPO26589793, ISSN: 0003-2670, DOI: 10.1016/S0003-2670 (00) 87832-0 [retrieved on Jan. 1, 1995] abstract.
Macmillan et al: "A reproducible method for determination of nitrocellulose in soil", Talanta, Elsevier, Amsterdam,NL vol. 70, No. 4, Jan. 2, 2008, pp. 1026-1031, XPO22405998, ISSN:0039-9140 abstract pp. 1028, lines 32-35.
Lopez-Lopez M et al: "Determination of the nitrogen content of nitrocellulose from smokeless gunpowders and collodions by alkaline hydrolysis and ion chromatography", Analytica Chimica Acta, Elsevier, Amsterdam, NL, vol. 685, No. 2, Jan. 31, 2011, pp. 196-203, XPO27563035, ISSN: 0003-2670 [retrieved on Dec. 16, 2010] abstract pp. 198, left-hand column.

* cited by examiner

*Primary Examiner* — Monique Cole
(74) *Attorney, Agent, or Firm* — Vidas, Arrett & Steinkraus, P.A.

(57) ABSTRACT

In at least one embodiment, the invention is directed to a method of determining the nitrogen content in nitrocellulose by High Performance Liquid Chromatography (HPLC). It is within the scope of the invention for the sample of nitrocellulose to be unstable nitrocellulose, unrefined nitrocellulose, or refined nitrocellulose. The sample of nitrocellulose can wet or dry. A sample of nitrocellulose that is wet can be in acid or in water. Before HPLC, the sample is dissolved in a suitable solvent. The nitrogen content of the sample is determined by comparing the retention time of the sample to a graph of retention time to amount of nitrogen due to the linear correlation of retention time and percent nitrogen substitution.

20 Claims, 6 Drawing Sheets

METHODOLOGY FOR DETERMINATION OF NITROGEN CONTENT IN NITROCELLULOSE

CROSS-REFERENCE TO RELATED APPLICATIONS

Not Applicable

STATEMENT REGARDING FEDERALLY SPONSORED RESEARCH

Not Applicable

FIELD OF THE INVENTION

The invention relates to the determination of nitrogen content in samples of unstable nitrocellulose, unrefined nitrocellulose, or refined nitrocellulose.

BACKGROUND OF THE INVENTION

Nitrocellulose, also known as cellulose nitrate, is used for several different purposes. For example, nitrocellulose is used in explosive and as propellant for guns and rockets. For entertainment, nitrocellulose is used to make magician's "flash paper." In biotechnology, nitrocellulose membranes or papers are used to immobilize proteins for Western blots and to immobilize DNA for Southern blots.

Nitrocellulose is manufactured by using an acid, e.g. nitric acid ($HNO_3$), to convert cellulose into nitrocellulose and water. During the reaction sulfuric acid is generally used to prevent the water produced in the reaction from diluting the concentration of the nitrocellulose. The average formula of nitrocellulose can be represented as $C_6H_{(10-n)}O_5(NO_2)_n$ where $0<n \leq 3$, depending upon the degree of nitration. Commercial military grade nitrocellulose is manufactured to specific nitrogen contents based on the product requirements.

BRIEF SUMMARY OF THE INVENTION

In at least one embodiment, the invention is directed to a method of determining the nitrogen content in nitrocellulose by High Performance Liquid Chromatography (HPLC). It is within the scope of the invention for the sample of nitrocellulose to be unstable nitrocellulose, unrefined nitrocellulose, or refined nitrocellulose. The sample of nitrocellulose can be wet or dry. A sample of nitrocellulose that is wet can be in acid or in water. Before HPLC the sample is dissolved in a suitable solvent. The nitrogen content of the sample is determined by comparing the retention time of the sample to a graph of retention time to amount of nitrogen due to the linear correlation of retention time and percent nitrogen substitution.

DETAILED DESCRIPTION OF THE INVENTION

Figure 1:
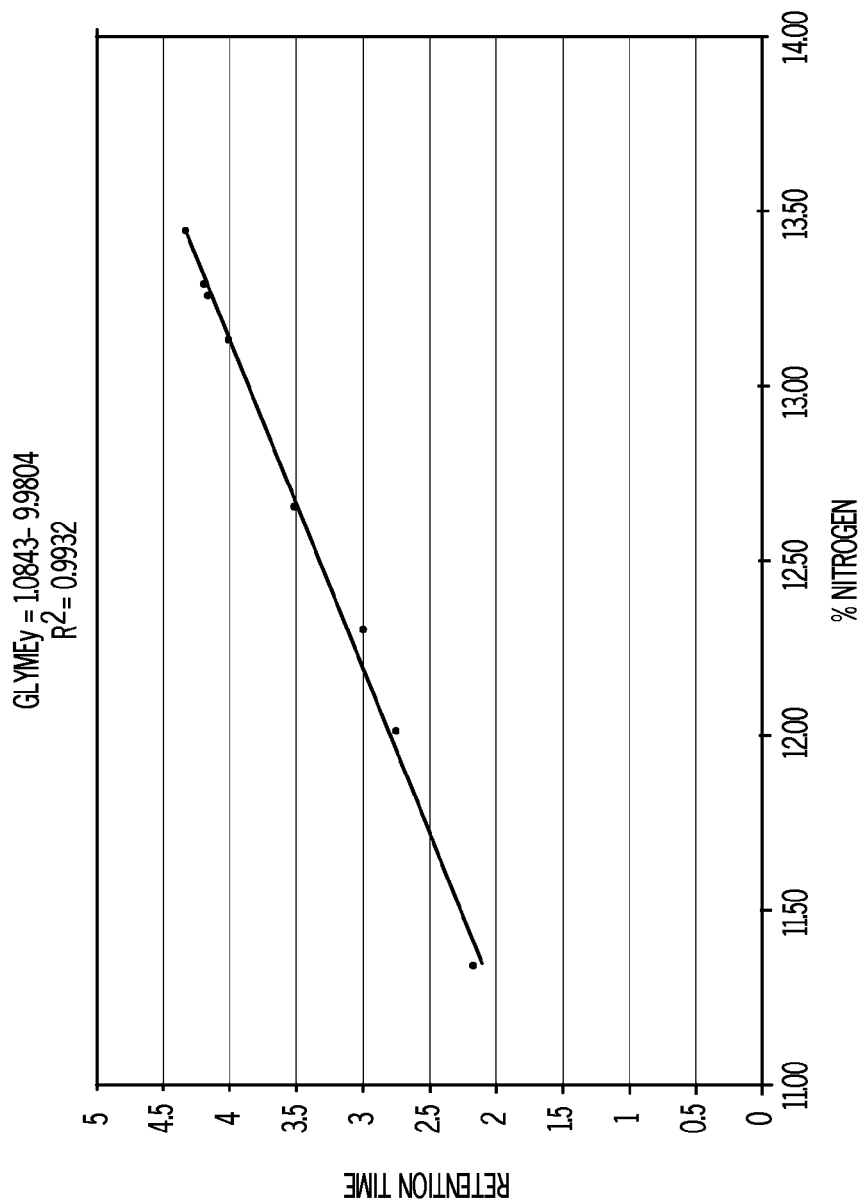
FIG. 1 is a graph of nitrogen versus retention time for nitrocellulose in 1,2-dimethoxyethane.

While this invention may be embodied in many forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In at least one embodiment, the invention is directed towards a method of analyzing the nitrogen content of nitrocellulose. It is within the scope of the invention for the nitrocellulose to be made from any cellulose material, including but not limited to wood pulp, sheeted cotton linters and bailed cotton linters. It is within the scope of the invention for the HPLC analysis to be done on a sample of nitrocellulose that is unstable nitrocellulose, unrefined nitrocellulose, or refined nitrocellulose. The sample of nitrocellulose can be wet or dry. A sample of nitrocellulose that is wet can be either in acid or in water. In some embodiments, the nitrocellulose is unrefined. Thus, the determination of the nitrogen content in this embodiment can occur before the nitrocellulose is refined. In other embodiments, the nitrocellulose is refined. In at least one embodiment, the nitrocellulose nitrogen content of propellant samples is analyzed.

In at least one embodiment, the invention is directed towards using High Performance Liquid Chromatography (HPLC) to measure the nitrogen content of a sample of nitrocellulose that has an average formula of $C_6H_{(10-n)}O_5(NO_2)_n$ where $2<n \leq 3$. In this embodiment, the HPLC separates nitrocellulose based on macromolecular functionality. In some embodiments, the HPLC method is applicable to nitrocellulose containing more than 11% nitrogen (w/w). In other embodiments, nitrocellulose containing between about 11% to about 14% nitrogen can be analyzed by the inventive HPLC method.

In at least one embodiment, a sample of nitrocellulose is dissolved in a suitable solvent. Examples of suitable solvents, include, but are not limited to, 1,2-dimethoxyethane, acetone, ethyl acetate, tetrahydrofuran, butyl acetate, acetone/water, 2-butanone, and acetonitrile. As discussed above, the sample of nitrocellulose can be unstable, unrefined, or refined and can be either wet or dry. Note that if the sample of nitrocellulose is a wet sample that is unstable or unrefined, the sample of nitrocellulose is merely diluted in a suitable solvent. Thus, no drying of the sample of the nitrocellulose is required before HPLC.

Once the sample of nitrocellulose is dissolved in the solvent, the sample is analyzed using HPLC. It is within the scope of the invention for any HPLC system to be used to analyze the sample of nitrocellulose. In at least one embodiment, a reversed phase column is used in the HPLC analysis. Such systems employ a relatively non-polar stationary phase and a relatively polar mobile phase. Silica treated to provide a large hydrocarbon group (e.g. a $C_{6-30}$ alkyl group) on the surface may provide suitable stationary phases. Examples of suitable reversed phase columns, include, but are not limited to, monolithic octadecyl silica (e.g., Onyx™ C18 columns from Phenomonex), spherical octadecyl silica (e.g., Microsorb MV C18 columns from Varian or Rainin) and spherical octyl silica (e.g., Microsorb MV C8 columns from Varian or Rainin).

In at least one embodiment, the solvent system for the HPLC is polar. In some embodiments, the HPLC solvent is provided in a gradient over time. In at least one embodiment, the HPLC solvent is an acetonitrile/water gradient system, e.g. one that begins at 85/15 volume/volume acetonitrile/water and changes to 100% acetonitrile over a 5 minute linear gradient with a flow rate of about 1.5 ml/min. It is also within the scope of the invention for the HPLC solvent to be a 1,2-dimethoxyethane/water gradient system or an acetone/water gradient system.

It is within the scope of the invention for any detector capable of detecting nitrocellulose to be used. In at least one embodiment, the detection is by ultraviolet light at 210 nm. The nitrate functionality of nitrocellulose absorbs at 210 nm while acetonitrile has low absorbance at 210 nm. In some embodiments, evaporative light scattering is used to detect the nitrocellulose.

A correlation of the percentage of nitrogen versus peak retention time for the HPLC method is suitably established against a primary method standard. In some embodiments the correlation is linear over the typical range of nitrogen content found in explosive grades of nitrocellulose. In some embodiments, the primary method is ferrous sulfate titration. An exemplary such primary method is MIL-STD-286C method 209.11.1, as described in Propellants, Solid: Sampling, Examination and Testing, distributed by the Department of Defense, incorporated by reference. Thus, when a sample is analyzed by HPLC, the retention time at the maximum of each peak can be compared to the correlation obtained by the primary method to determine the nitrogen content of the sample. Measured against such primary standard, in at least some embodiments, the inventive method is able to distinguish nitrogen content to an accuracy of about ±0.10% or better.

In addition to providing an accurate measurement of the nitrogen content of a nitrocellulose sample, insights into nitration distribution can be obtained from the HPLC chromatogram. In particular it is believed that the peak symmetry and peak width are indicative of the nitration characteristics of the sample. Since the percent nitrogen is determined based on the retention time of the peak maximum, any peak asymmetry (i.e. deviation from a normal distribution about the peak maximum) gives an indication of a non-uniformity in the nitrogen content of the different molecules making up the nitrocellulose sample. This non-uniformity can give an indication to the process conditions present to produce such a distribution. In a similar manner, it is thought that peak width provides an estimated measure of the range of nitrogen content between the different molecules making up the nitrocellulose sample. Thus, it is thought that both of these chromatographic parameters, peak asymmetry and peak width, provide information on the make-up of the nitrocellulose sample being measured that is not available from the primary method nitrogen content measurement.

Experimental Results

Figure 2:
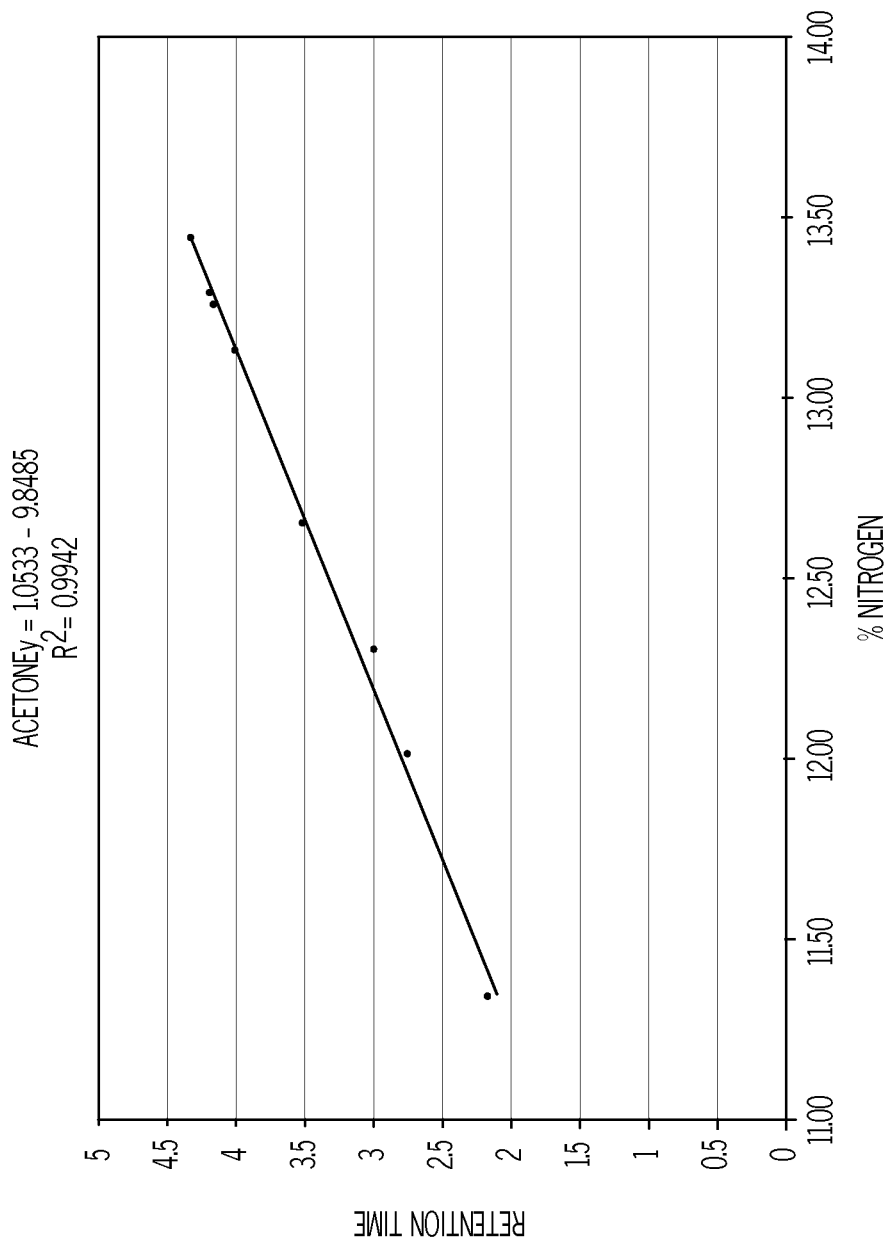
FIG. 2 is a graph of nitrogen versus retention time for nitrocellulose in acetone.

FIGS. 1 and 2 are two graphs of nitrogen versus retention time for nitrocellulose in 1,2-dimethoxyethane (glyme) and for nitrocellulose in acetone. As discussed above, using the primary method, the nitrogen content of a sample can be determined by the HPLC retention time(s) of the sample. The HPLC retention time(s) of the sample is measured from the maximum height of the peak(s).

Figure 3:
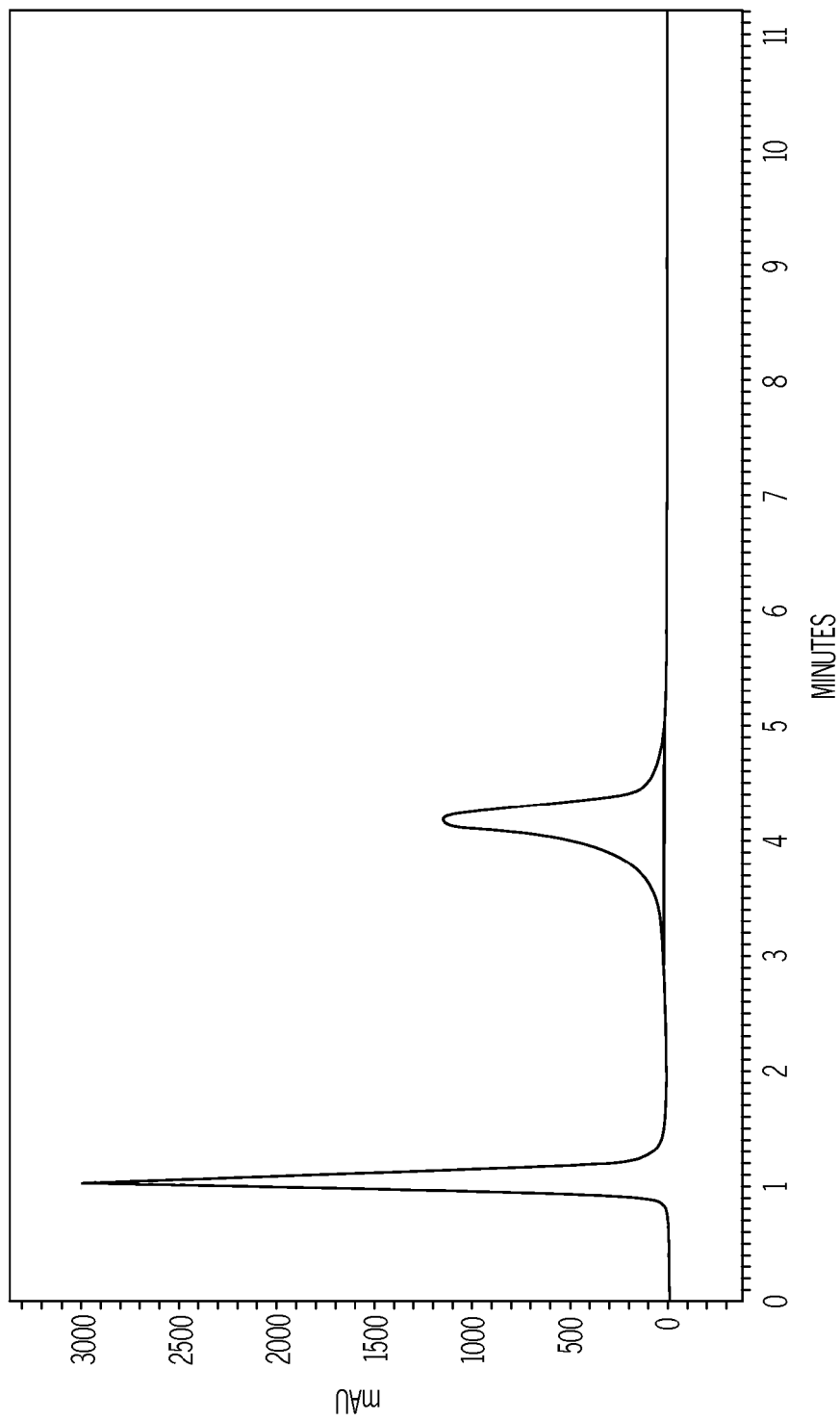
FIG. 3 is a HPLC chromatograph of a sample of nitrocellulose.

The following table compares the results obtained for four samples with that were analyzed using a FeSO4 primary method (MIL-STD-286C, method 209.11.1), and then using the HPLC method. FIG. 3 is the HPLC chromatogram for the TS955 P1 PO20 sample. As shown by column 5 of the table, the Difference column, the results obtained using the inventive HPLC method are similar to the results obtained by ferrous sulfate titration.

| Sample ID | Analysis of Sample with FeSO$_4$ | HPLC Retention Time | Estimated nitrogen content based on retention time | Difference between HPLC method and primary method |
|---|---|---|---|---|
| TL946 P1 PO3 | 13.45 | 4.323 | 13.45 | 0.00 |
| TS955 P1 PO20 | 13.32 | 4.202 | 13.34 | 0.02 |
| TS10558Y T27 | 13.12 | 4.051 | 13.20 | 0.08 |
| TS10560Y T30 | 13.18 | 4.070 | 13.21 | 0.03 |

Figure 4:
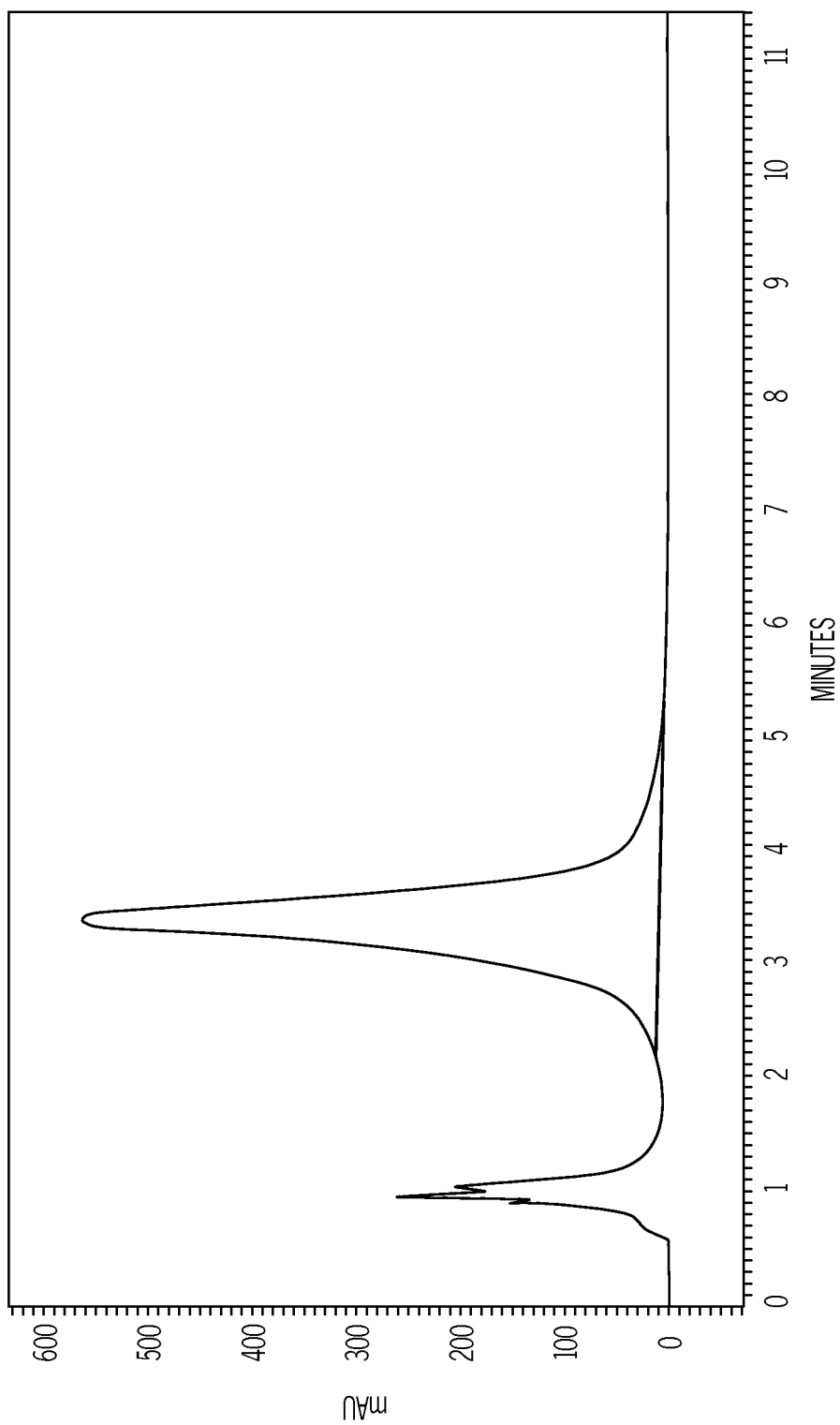
FIG. 4 is a HPLC chromatograph of a sample of nitrocellulose.
Figure 5:
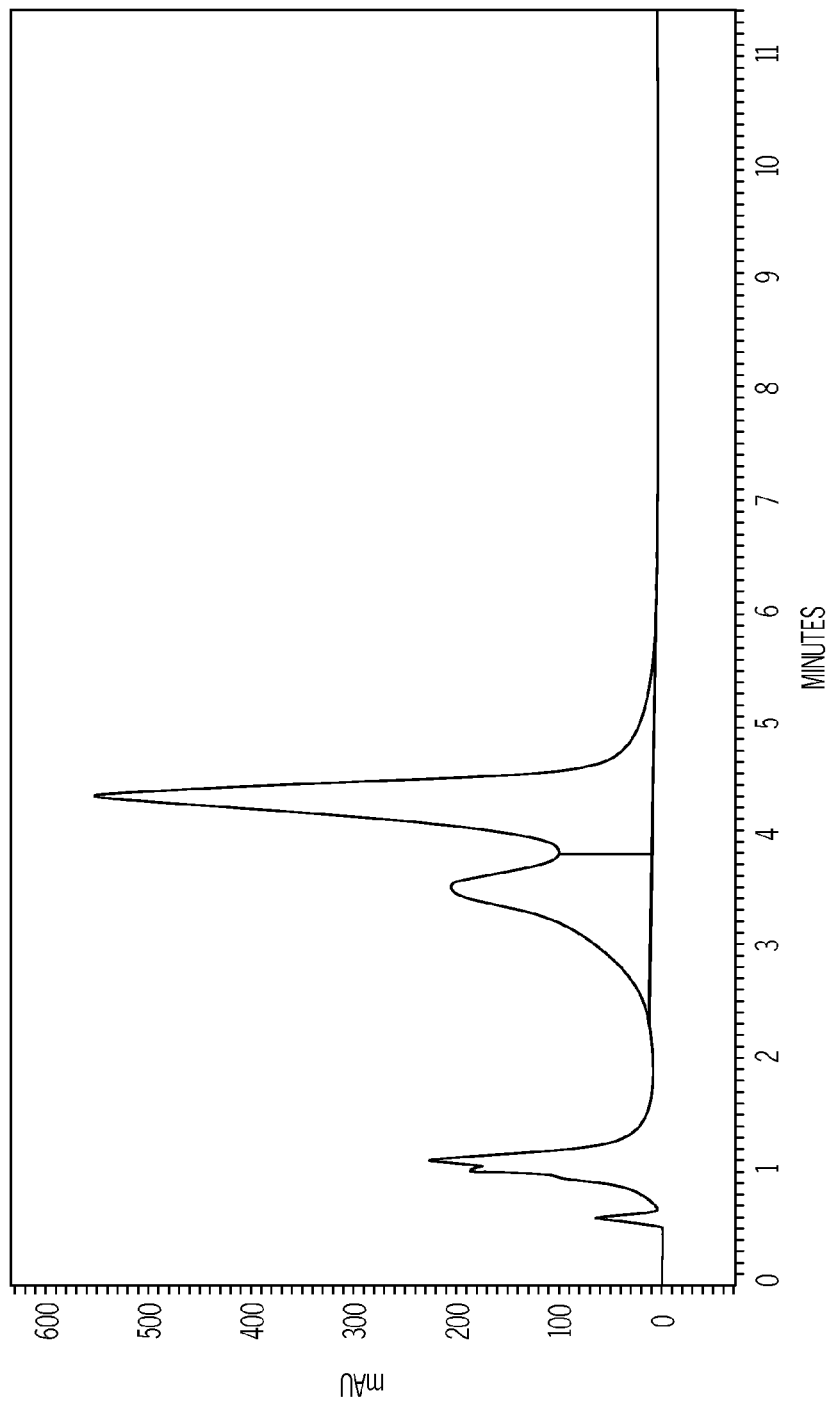
FIG. 5 is a HPLC chromatograph of a two-component sample of nitrocellulose.
Figure 6:
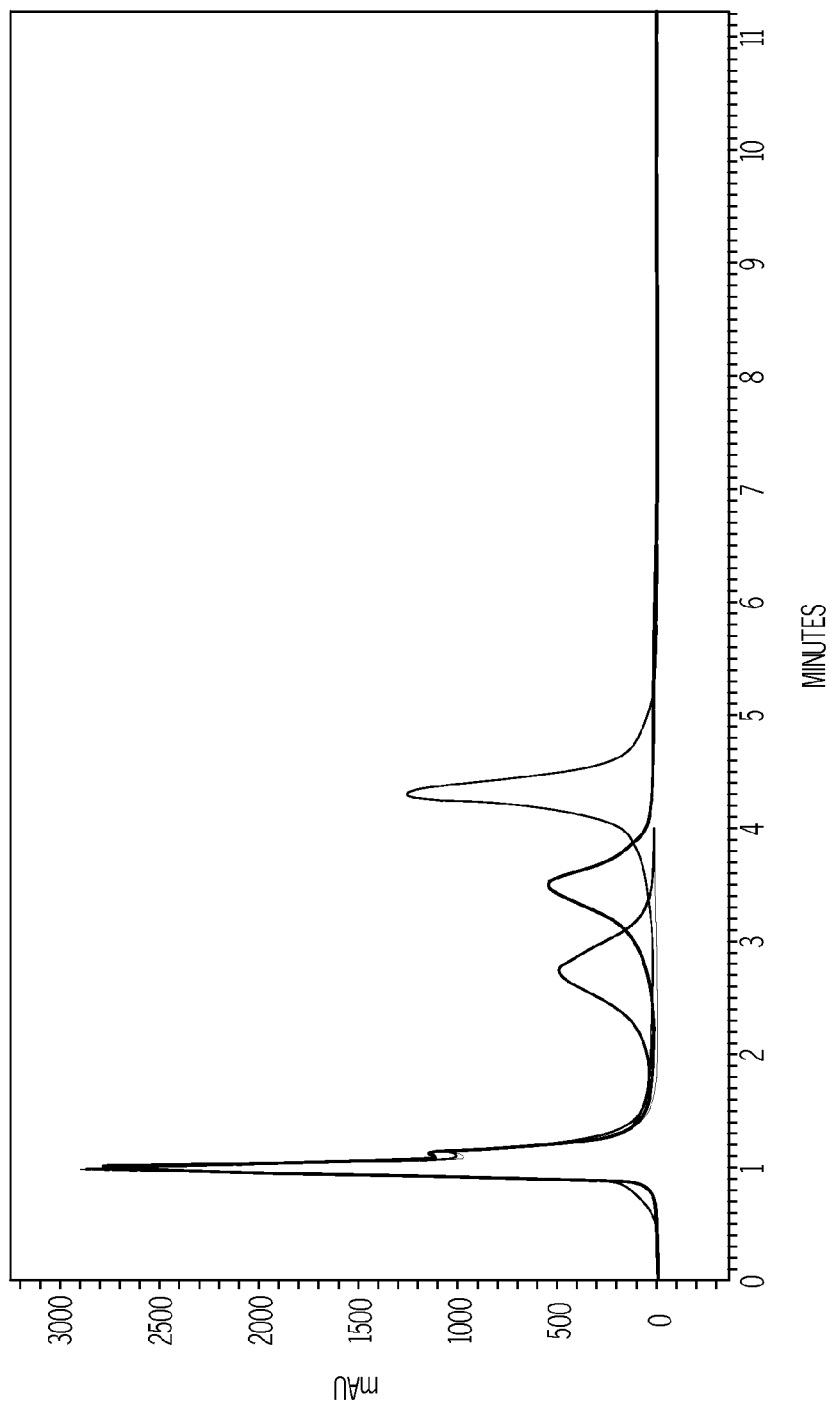
FIG. 6 is an overlay of HPLC chromatograms of three samples of nitrocellulose that have different percentages of nitrogen.

FIGS. 4-6 are HPLC chromatograms of samples of nitrocellulose. In FIG. 4, the sample of nitrocellulose, BG34019, has 12.52% nitrogen. FIG. 5 is a HPLC chromatogram of a two component sample of nitrocellulose. Thus, the first peak corresponds to a first component of the nitrocellulose sample that has 12.7% nitrogen and the second peak corresponds to a second component of the nitrocellulose sample that has 13.3% nitrogen. The overlay of three HPLC chromatograms in FIG. 6 shows that samples of nitrocellulose with different percentages of nitrogen can be differentiated by their HPLC retention time. The samples of nitrocellulose have 12.00% nitrogen, 12.64% nitrogen and 13.64% nitrogen. As shown in FIG. 6, the retention times increase as the percentage of nitrogen in the sample increases.

What is claimed is:

1. A method comprising
subjecting a sample of nitrocellulose to HPLC; and
determining the nitrogen content of the sample of nitrocellulose as a function of HPLC retention time of the sample of nitrocellulose.

2. The method of claim 1, wherein the nitrocellulose is selected from the group consisting of refined nitrocellulose, unstable nitrocellulose, or unrefined nitrocellulose.

3. The method of claim 2, wherein the nitrocellulose is wet.

4. The method of claim 1, wherein the sample of nitrocellulose is dissolved in a solvent is selected from the group consisting of 1,2-dimethoxyethane, acetone, ethyl acetate, tetrahydrofuran, butyl acetate, acetone/water, 2-butanone, acetonitrile, and any combination thereof.

5. The method of claim 1, the HPLC being reversed phase HPLC.

6. The method of claim 5, the reversed phase HPLC using a column having as its stationary phase a silica treated to provide $C_{6-30}$ alkyl groups on the surface thereof.

7. The method of claim 5, the reversed phase HPLC using a polar solvent system.

8. The method of claim 7, the HPLC solvent system is a gradient solvent system changing over a time period in which HPLC is performed.

9. The method of claim 7, the HPLC solvent system being an acetonitrile/water solvent system.

10. The method of claim 9, wherein the ratio of acetonitrile to water is changed over a time period in which the HPLC is performed.

11. The method of claim 10, the ratio changes as a linear gradient of 85/15 (v/v) acetonitrile/water to 100% acetonitrile over said time period.

12. The method of claim 7, the HPLC solvent system being a 1,2-dimethoxyethane water solvent system.

13. The method of claim 7, the HPLC solvent system being an acetone/water solvent system.

14. The method of claim 1, further comprising correlating the HPLC retention time of the sample of nitrocellulose to nitrogen content of the sample of nitrocellulose to a graph of nitrogen content and HPLC retention time of reference samples of nitrocellulose.

15. The method of claim 14, wherein the nitrogen content of the reference samples of nitrocellulose is determined by ferrous sulfate titration.

16. The method of claim 14, wherein the nitrogen content of reference samples of nitrocellulose is determined by MIL-STD-286C method 109.11.1.

17. The method of claim 1, the HPLC generating a chromatogram, the chromatogram comprising at least one peak, the at least one peak having a peak maximum, the peak maximum having a HPLC retention time, the HPLC retention time being used to determine the nitrogen content of the sample of nitrocellulose.

18. The method of claim 17, wherein a non-uniformity of an average nitrogen content of the sample of nitrocellulose can be determined by a deviation from an even distribution about the peak maximum.

19. The method of claim 17, the at least one peak having a peak width, the peak width providing an estimated measure of a distribution of the nitrogen content of the sample of nitrocellulose.

20. A method of analyzing nitrogen content of a sample of nitrocellulose comprising:

HPLC analysis of the sample of nitrocellulose, the HPLC analysis generating a chromatogram, the chromatogram comprising at least one peak with a peak maximum, the peak maximum having a retention time; and correlating the retention time of the peak maximum to the nitrogen content of the sample of nitrocellulose by comparing the retention time of the peak maximum to a graph of retention time and nitrogen content of reference samples of nitrocellulose.

* * * * *